United States Patent
Davis

(10) Patent No.: US 11,154,621 B2
(45) Date of Patent: Oct. 26, 2021

(54) LIPONUCLEOTIDE-BASED THERAPY FOR COPD

(71) Applicant: Ohio State Innovation Foundation, Columbus, OH (US)

(72) Inventor: Ian Christopher Davis, Hilliard, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/626,434

(22) PCT Filed: Jun. 27, 2018

(86) PCT No.: PCT/US2018/039655
§ 371 (c)(1),
(2) Date: Dec. 24, 2019

(87) PCT Pub. No.: WO2019/005898
PCT Pub. Date: Jan. 3, 2019

(65) Prior Publication Data
US 2020/0129623 A1    Apr. 30, 2020

Related U.S. Application Data

(60) Provisional application No. 62/525,341, filed on Jun. 27, 2017.

(51) Int. Cl.
*A61K 31/66* (2006.01)
*A61K 47/54* (2017.01)
*A61P 11/00* (2006.01)

(52) U.S. Cl.
CPC ............ *A61K 47/543* (2017.08); *A61K 31/66* (2013.01); *A61P 11/00* (2018.01)

(58) Field of Classification Search
CPC ........ A61K 47/543; A61K 31/66; A61P 11/00
See application file for complete search history.

(56) References Cited

U.S. PATENT DOCUMENTS 7,105,498 B2 * 9/2006 von Borstel ......... A61K 31/513
514/49
2003/0087845 A1 * 5/2003 Nyce ..................... A61K 31/00
514/44 R (Continued)

FOREIGN PATENT DOCUMENTS

WO    2018005527 A1    1/2018

OTHER PUBLICATIONS

Matera, M. G., et al in Pulmonary Pharmacology & Therapeutics, vol. 23, pp. 121-128, 2010.*

(Continued)

*Primary Examiner* — Gollamudi S Kishore
(74) *Attorney, Agent, or Firm* — Thomas|Horstemeyer LLP

(57) ABSTRACT

Compositions and method are therefore disclosed for treating chronic obstructive pulmonary disease (COPD) and/or pulmonary fibrosis (PF). In particular, disclosed a composition that contains one, two, or more cytidine diphosphate (CDP)-conjugated phospholipid precursors selected from the group consisting of CDP-choline, CDP-ethanolamine, and CDP-diacylglycerol in a pharmaceutically acceptable carrier for use in treating COPD and/or PF.

9 Claims, 11 Drawing Sheets

(56) References Cited

U.S. PATENT DOCUMENTS

| | | | |
|---|---|---|---|
| 2005/0220859 A1* | 10/2005 | Frankenberger | A61K 9/127 424/450 |
| 2007/0021360 A1 | 1/2007 | Nyce | |
| 2014/0200332 A1* | 7/2014 | Kaymakcalan | A61P 1/00 530/388.15 |
| 2015/0246119 A1 | 9/2015 | Pirozzi et al. | |
| 2015/0335716 A1* | 11/2015 | Settineri | A61K 9/0056 424/441 |
| 2016/0058873 A1* | 3/2016 | Fetzer | A61K 38/08 514/1.3 |
| 2017/0173065 A1 | 6/2017 | Kwon et al. | |

OTHER PUBLICATIONS

Traylor et al., Respiratory syncytial virus induces airway insensitivity to β-agonists in BALB/c mice, Am J Physiol Lung Cell Mol Physiol 298: L437-L445, 2010.

Yoshida et al., Annexin V decreases PS-mediated macrophage efferocytosis and deteriorates elastase-induced pulmonary emphysema in mice, Am J Physiol Lung Cell Mol Physiol 303: L852-L860, 2012.

International Search Report issued for PCT/US2018/039655, dated Sep. 18, 2018.

International Search Report issued for PCT/US2018/039658, dated Sep. 19, 2018.

International Search Report issued from the European Patent Office for application EP18825026, dated Mar. 2, 2021.

Davis et al., Post-Infection 1-10 Treatment with Liponucleotides Attenuates H1N1 Influenza A Virus-Induced ARDS in Mice, ATS Journals, 195:A2920, 2017.

Davis et al., Post-Infection Treatment with Liponucleotides, ATS Journals, 195:A2920, 2017.

Cetinkaya et al., Cytidine 5'-diphosphocholine ameliorates hyperoxic lung injury in a neonatal rat model, Pediatric Research, vol. 74, No. 1, p. 26-33, 2013.

Pacheco et al., Respiratory function and alveolar biological changes under the effect of CDP-choline in pulmonary interstitial pathology: pulmonary fibrosis and sarcoidosis, Rev. Pneumol Clin. 41(2)91-100, 1985.

American Thoracic Society International Conference, Final Program, ATS 2017, May 19-May 24, 2017 Washington, DC.

* cited by examiner

LIPONUCLEOTIDE-BASED THERAPY FOR COPD

CROSS-REFERENCE TO RELATED APPLICATIONS

This application claims benefit of U.S. Provisional Application No. 62/525,341, filed Jun. 27, 2017, which is hereby incorporated herein by reference in its entirety.

BACKGROUND

Chronic obstructive pulmonary disease (COPD) is currently the third leading cause of mortality worldwide. Smoking (primarily of cigarettes, but also of marijuana or from hookahs) is the primary cause of COPD. However, COPD can also result from chronic exposure to air pollution, products of combustion, and environmental or occupational irritant vapors. Effects of these agents are exacerbated by age and poor nutrition. Poor lung development (in utero or during childhood), genetic α1-antitrypsin deficiency, and starvation can also lead to COPD. In some cases, there is an overlap between signs and symptoms of COPD and those of asthma. Finally, COPD can increase susceptibility to viral and bacterial infections, which may result in significant and sometimes life-threatening disease exacerbations.

Emphysema and chronic bronchitis, which can be present to varying degrees in individual patients, are the hallmarks of COPD and together result in restriction of airflow, mild hypoxemia, frequent and often productive coughing, and exercise intolerance. Current therapeutic options are limited, and primarily ameliorate symptoms rather than prevent or reverse disease progression. Patients with COPD frequently require supplemental oxygen (usually delivered via nasal cannula) and may be prescribed inhalers containing corticosteroids and/or short- or long-acting β-adrenergic agonists (which have anti-inflammatory and bronchodilatory effects) for use as needed.

Pulmonary fibrosis (PF) is an interstitial lung disease involving gradual exchange of normal lung parenchyma with fibrotic tissue as a result of perpetuating aberrant wound healing. The replacement of normal lung with scar tissue causes irreversible decrease in oxygen diffusion capacity, and the resulting stiffness or decreased compliance makes PF a restrictive lung disease. Severe fibrosis can also result in pulmonary hypertension and right heart failure. Treatment options are very limited. Anti-inflammatory drugs are effective in some patients, and anti-scarring agents (pirfenidone and nintedanib) may be of value in mild PF. Many patients require supplemental oxygen and in severe cases lung transplantation may be the only option.

PF can develop in the absence of any known cause, in which case it is usually referred to as idiopathic pulmonary fibrosis (IPF). PF can also be a secondary effect of other diseases that cause lung damage and scarring. These include exposure to and inhalation of environmental and occupational pollutants, such as asbestos, silica, heavy metals, volatile organic compounds (including, but not limited to paint, varnishes, cleaners, cosmetics, pesticides, and flavoring agents) and diesel particulates. Additional causes of PF include: 1) severe lung injury (e.g., ARDS); 2) hypersensitivity pneumonitis (usually a result of inhaling dust contaminated with bacterial, fungal, or animal products); 3) connective tissue diseases (e.g., rheumatoid arthritis, systemic lupus erythematosis, scleroderma, sarcoidosis, and granulomatosis with polyangiitis); 4) severe acute or chronic infections; 5) medications including amiodarone, bleomycin, busulfan, methotrexate, apopmorphine, and nitrofurantoin; 6) thoracic radiation therapy; and 7) genetic abnormalities. Cigarette smoking can exacerbate progression of PF and the pathogenic events underlying development of PF share many commonalities with those underlying COPD (including, but not limited to, respiratory epithelial cell mitochondrial dysfunction, oxidative stress, and endoplasmic reticulum stress, epithelial-to-mesenchymal transition, alterations in the protease/anti-protease balance, macrophage dysregulation, and chronic inflammation caused by repeated respiratory tract infections).

SUMMARY

COPD has been associated with disruption of pulmonary surfactant phospholipid (Plipid) homeostasis, and results in reductions in surfactant Plipids in bronchoalveolar lavage (BALF) from smokers, alveolar type II (ATII) cell phosphatidylcholine (PC) content, and ATII cell PC secretion in vitro. In addition, emphysema results in a reduction in total numbers of ATII cells in the lung. These data suggest that de novo Plipid synthesis by ATII cells may be impaired in patients with COPD and amenable to treatment with liponucleotides.

Epithelial to mesenchymal transition is a hallmark of PF. Consequently ATII cell numbers are reduced in the PF lung, and experimental depletion of ATII cells induces spontaneous fibrosis in mice. PF has also been shown to result in reduce BALF Plipid (PC and PG) and abnormal surfactant function in mice with bleomycin-induced PF and in patients with hypersensitivity pneumonitis, sarcoidosis, and IPF. Hence, treatment with liponucleotides could improve surfactant and lung function by enhancing de novo Plipid synthesis by ATII cells.

Compositions and methods are therefore disclosed for preventing, retarding development of, or treating COPD and/or PF. For example, a composition is disclosed that contains one, two, or more cytidine diphosphate (CDP)-conjugated phospholipid precursors selected from the group consisting of CDP-choline (CDP-CHO), CDP-ethanolamine (CDP-ETH), and CDP-diacylglycerol (CDP-DAG) in a pharmaceutically acceptable carrierr.

Diacylglycerol (DAG) is a glyceride consisting of two fatty acid chains covalently bonded to a glycerol molecule through ester linkages. Two possible forms exist, 1,2-diacylglycerols and 1,3-diacylglycerols. In some embodiments, the CDP-DAG contains short-chain fatty acids (with aliphatic tails containing fewer than 6 carbons), medium-chain fatty acids (with aliphatic tails containing 6-12 carbons), long-chain fatty acids (with aliphatic tails containing 13-21 carbons), or very long-chain fatty acids (with aliphatic tails containing more than 22 carbons). Fatty acids may be of natural origin or generated by chemical synthesis, according to any methods known to those skilled in the art. In some embodiments, the two fatty acid chains are in the 1,2 positions. In some embodiments, the two fatty acid chains are in the 1,3 positions. In some embodiments, both fatty acid chains are of the same length (contain the same number of carbons). In some embodiments, the two fatty acid chains are of different lengths. In some embodiments, one or both fatty acid chains of the DAG component of CDP-DAG are mono-unsaturated (containing one double bond in cis and/or trans configuration). In some embodiments, one or both fatty acid chains of the DAG component of CDP-DAG are poly-unsaturated (containing more than one double bond in cis and/or trans configuration). In some embodiments, one or both fatty acid chains of the DAG component of CDP-DAG are saturated (containing no double bonds). In some embodiments, one or both fatty acid chains are chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-CHO is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-ETH is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-DAG is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the choline component of CDP-CHO is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the ethanolamine component of CDP-ETH is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the glycerol component of CDP-DAG is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, a mixture of two or more CDP-CHO-derived Plipid precursors with or without different chemical modifications of CDP and/or choline can be incorporated.

In some embodiments, a mixture of two or more CDP-ETH-derived Plipid precursors with or without different chemical modifications of CDP and/or ethanolamine chains can be incorporated.

In some embodiments, a mixture of two or more CDP-DAG-derived Plipid precursors with or without different acylations or chemical modifications of CDP and/or fatty acid chains can be incorporated.

In some embodiments, the CDP-conjugated Plipid precursors are collectively present at a unit dose of at least 0.1 ng/kg, including 0.1, 0.2, 0.3, 0.4, 0.5, 0.6, 0.7, 0.8, 0.9, 1.0 ng/kg.

In some embodiments, the CDP-CHO and/or CDP-ETH and/or CDP-DAG are present in equal concentrations or ratios. In some embodiments, at least two of the CDP-conjugated Plipid precursors are present in equal concentrations or ratios, which can be higher or lower than the third CDP-conjugated Plipid precursor, which may be absent. In some cases, one of the CDP-conjugated Plipid precursors is present at a concentration or ratio that is at least 2, 3, 4, 5, 6, 7, 8, 9, or 10 fold higher than one or both of the other CDP-conjugated Plipid precursors.

The disclosed compositions can further contain other active and inactive ingredients. For example, in some embodiments, the composition can contain additional lipid moieties, nucleotides, organic acids, amino acids, or sugars. The composition can also contain a stabilizer.

Also disclosed is a method treating for treating or preventing development of COPD and/or PF in a subject that involves administering to the subject an effective amount of a composition comprising a CDP-conjugated precursor selected from the group consisting of CDP-CHO, CDP-ETH, CDP-DAG, and combinations thereof as prophylaxis prior to infection with one or more influenza virus strains.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a plot showing effect of infection on ATII cell DPPC (16:0/16:0) surfactant. #=P<0.001.

FIG. 2 is a plot showing effect of infection on ATII cell DPPG (16:0/16:0) surfactant. *=P<0.05, #=P<0.001.

FIG. 3 is a plot showing effect of infection on ATII cell PE (16:0/18:2) surfactant. #=P<0.001.

FIG. 4 is a plot showing effect of infection on BALF phospholipid glycerol. #=P<0.001.

FIG. 5 is a schematic showing DPPC synthesis by the CDP-choline (Kennedy) pathway.

FIG. 6 is a plot showing effect of infection on ATII cell DAG (18:1/18:2). *=P<0.05, #=P<0.001.

FIG. 7 is a plot showing effect of infection on ATII cell choline-P (18:1/18:2).

FIG. 8 is a plot showing effect of infection on ATII cell CDP-choline.

FIG. 9 is a schematic showing therapeutic approach.

FIG. 10 is a graph showing effect of CDP-choline treatment (▲) on mouse $O_2$ SATS as a function of time (days after infection). #=P<0.001.

FIG. 11 is a graph showing effect of CDP-choline treatment (▲) on mouse activity (rmp/mouse) as a function of time (days after infection). *=P<0.05, #=P<0.001.

FIG. 12 is a bar graph showing effect of day 5 only CDP-choline treatment on mouse $O_2$ SATS. *=P<0.05, #=P<0.001.

FIG. 13 is a bar graph showing effect of formulation treatment on mouse $O_2$ SATS. #=P<0.001.

FIG. 14 is a group of three transmission electron micrographs showing effects of CDP-choline treatment on ultrastructure of ATII cell lamellar bodies (composed of surfactant lipids and proteins).

FIG. 15 is a group of 3 transmission electron micrographs showing effects of influenza infection on ultrastructure of ATII cell mitochondria (Mi).

FIG. 16 is a bar graph showing the effect of treatment with CDP-CHO alone, CDP-CHO+CDP-ETH, CDP-CHO+CDP-DAG, and CDP-CHO+CDP-ETH+CDP-DAG from days 1-13 on static lung compliance (CST). UNTx: Elastase only (no lipoNT treatment). Data shown as mean±standard error of mean (SEM). *: $P<0.05$, **: $P<0.005$, vs. normal mice. ‡: $P<0.005$, vs. CDP-CHO.

FIG. 17 is a bar graph showing effect of treatment with CDP-CHO alone, CDP-CHO+CDP-ETH, CDP-CHO+ CDP-DAG, and CDP-CHO+CDP-ETH+CDP-DAG from days 1-13 on bronchoalveolar lavage fluid (BALF) alveolar macrophages (AMs). UNTx: Elastase only (no lipoNT treatment). Data shown as mean±SEM. *:$P<0.05$, vs. UNTx.

FIG. 18 is a bar graph showing effect of treatment with CDP-CHO+CDP-ETH and CDP-CHO+CDP-DAG from days 8-13 on static lung compliance (CST). UNTx: Elastase only (no lipoNT treatment). Data shown as mean±standard error of mean (SEM). *: $P<0.05$, **: $P<0.005$, vs. normal mice.

FIG. 19 is a bar graph showing effect of treatment with CDP-CHO+CDP-ETH or CDP-CHO+CDP-DAG from days 8-13 on bronchoalveolar lavage fluid (BALF) alveolar macrophages (AMs). UNTx: Elastase only (no lipoNT treatment). Data shown as mean±SEM.

FIG. 20 is a bar graph showing effect of treatment with CDP-CHO alone and CDP-CHO+CDP-ETH from days 1-20 on lung soluble collagen content at day 21. Data shown as mean±SEM. *:$P<0.05$, vs. BLEO exposed untreated mice (UNTx). †: $P<0.05$, vs. CDP-CHO alone.

FIG. 21 is a bar graph showing effect of treatment with CDP-CHO alone and CDP-CHO+CDP-ETH from days 1-20 on static lung compliance (CST). UNTx: BLEO-exposed untreated mice. Data shown as mean±standard error of mean (SEM). **: $P<0.005$ vs. normal mice.

FIG. 22 is a bar graph showing effect of treatment with CDP-CHO+CDP-ETH from days 8-20 on lung soluble collagen content at day 21. Data shown as mean±SEM. *:$P<0.05$, vs. BLEO-exposed untreated mice (UNTx).

FIG. 23 is a bar graph showing effect of treatment with CDP-CHO alone and CDP-CHO+CDP-ETH from days 8-20 on static lung compliance (CST). UNTx: BLEO-exposed untreated mice. Data shown as mean±standard error of mean (SEM). *: $P<0.05$, **: $P<0.005$ vs. normal mice.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "subject" refers to any individual who is the target of administration or treatment. The subject can be a vertebrate, for example, a mammal or bird. Thus, the subject can be a human or veterinary patient. The term "patient" refers to a subject under the treatment of a clinician, e.g., physician or veterinarian, as well as other allied health professionals, including (but not limited to) nurses, physician's assistants, and pharmacists.

The term "therapeutically effective" refers to the amount of the composition used is of sufficient quantity to ameliorate one or more causes, symptoms, and/or clinical signs of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms and/or clinical signs rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The disclosed methods can be used to prevent or treat any form of COPD and/or PF, irrespective of its underlying cause. COPD is a type of obstructive lung disease characterized by long-term breathing problems and poor airflow. The main symptoms include shortness of breath and cough with sputum production. Chronic bronchitis and emphysema are older terms used for different types of COPD. The term "chronic bronchitis" is still used to define a productive cough that is present for at least three months each year for two years.

Tobacco smoking is the most common cause of COPD, with factors such as air pollution and genetics playing a smaller role. The diagnosis is based on poor airflow as measured by lung function tests. In contrast to asthma, the airflow reduction does not improve much with the use of a bronchodilator.

The primary risk factor for COPD globally is tobacco smoking. Of those who smoke, about 20% will get COPD, and of those who are lifelong smokers, about half will get COPD. Poorly ventilated cooking fires, often fueled by coal or biomass fuels such as wood and dung, lead to indoor air pollution and are one of the most common causes of COPD in developing countries. These fires are a method of cooking and heating for nearly 3 billion people, with their health effects being greater among women due to more exposure. Intense and prolonged exposure to workplace dusts, chemicals, and fumes increases the risk of COPD in both smokers and nonsmokers. A number of industries and sources have been implicated, including high levels of dust in coal mining, gold mining, and the cotton textile industry, occupations involving cadmium and isocyanates, and fumes from welding. Working in agriculture is also a risk. Silica dust and fiberglass dust exposure can also lead to COPD, with the risk unrelated to that for silicosis. People who live in large cities have a higher rate of COPD compared to people who live in rural areas. Genetics also play a role in the development of COPD. Currently, the only clearly inherited risk factor is alpha-1 antitrypsin deficiency (AAT). This risk is particularly high if someone deficient in alpha-1 antitrypsin also smokes. An acute exacerbation of COPD is commonly triggered by infection or environmental pollutants, or sometimes by other factors such as improper use of medications.

The diagnosis of COPD should be considered in anyone over the age of 35 to 40 who has shortness of breath, a chronic cough, sputum production, or frequent winter colds and a history of exposure to risk factors for the disease. Spirometry is then used to confirm the diagnosis. COPD may need to be differentiated from other causes of shortness of breath such as pulmonary fibrosis (PF), congestive heart failure, pulmonary embolism, pneumonia, or pneumothorax. The distinction between asthma and COPD is made on the basis of the symptoms, smoking history, and whether airflow limitation is reversible with bronchodilators at spirometry. Tuberculosis may also present with a chronic cough and should be considered in locations where it is common. Less common conditions that may present similarly include bronchopulmonary dysplasia and obliterative bronchiolitis. Chronic bronchitis may occur with normal airflow and in this situation it is not classified as COPD.

PF is a respiratory disease in which scars are formed in the lung tissues, leading to serious breathing problems. Scar formation, the accumulation of excess fibrous connective tissue (the process called fibrosis), leads to thickening of the walls, and causes reduced oxygen supply in the blood. As a consequence patients suffer from perpetual shortness of breath. In some patients the specific cause of the disease can be diagnosed, but in others the probable cause cannot be determined, a condition called idiopathic pulmonary fibrosis (IPF).

Symptoms of PF include shortness of breath, particularly with exertion, chronic dry, hacking coughing, fatigue and weakness, chest discomfort including chest pain, and loss of appetite and rapid weight loss. PF is suggested by a history of progressive shortness of breath (dyspnea) with exertion. Sometimes fine inspiratory crackles can be heard at the lung bases on auscultation. A chest x-ray may or may not be abnormal, but high-resolution CT will frequently demonstrate abnormalities.

PF may be a secondary effect of other diseases. Most of these are classified as interstitial lung diseases. Examples include autoimmune disorders, viral infections and bacterial infection like tuberculosis which may cause fibrotic changes in both lungs upper or lower lobes and other microscopic injuries to the lung. Diseases and conditions that may cause pulmonary fibrosis as a secondary effect include: inhalation of environmental and occupational pollutants; hypersensitivity pneumonitis; cigarette smoking; connective tissue diseases, such as rheumatoid arthritis, SLE and scleroderma; other diseases that involve connective tissue, such as sarcoidosis and granulomatosis with polyangiitis; infections; certain medications, e.g. amiodarone, bleomycin (pingyangmycin), busulfan, methotrexate, apomorphine, and nitrofurantoin; and radiation therapy to the chest. Pulmonary fibrosis can also appear without any known cause. In this case, it is termed "idiopathic." Most idiopathic cases are diagnosed as IPF, which has a median survival of 3-5 years following diagnosis. IPF is a diagnosis of exclusion based on the presence of a characteristic set of histologic/pathologic features known as usual interstitial pneumonia (UIP), which is identified from a surgical lung biopsy, and/or the presence of specific findings by high-resolution computed tomography. In either case, there is a growing body of evidence which points to a genetic predisposition to pulmonary fibrosis in a subset of patients. For example, a mutation in surfactant protein C (SP-C) has been found to exist in some families with a history of pulmonary fibrosis. Moreover, the presence of co-morbidities associated with COPD (such as emphysema) can result in more rapid progression of IPF.

CDP-CHO is a naturally occurring compound that is synthesized from cytidine-5'-triphosphate and phosphocholine with accompanying production of inorganic pyrophosphate in a reversible reaction catalyzed by the enzyme CTP: phosphocholine cytidylyltransferase-α (pcyt1a). CDP-ETH is synthesized from cytidine-5'-triphosphate and phosphoethanolamine with accompanying production of inorganic pyrophosphate in a reversible reaction catalyzed by the enzyme CTP-phosphoethanolamine cytidyltransferase (pcyt2).

The molecular structure of CDP-CHO is provided below.

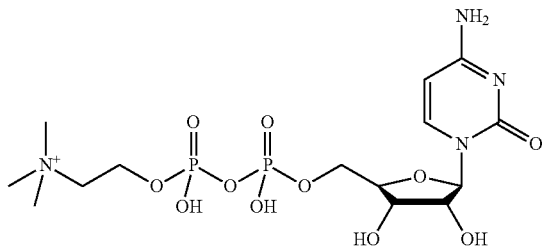

The molecular structure of CDP-ETH is provided below.

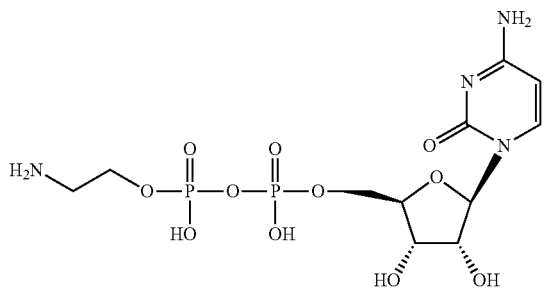 [SMILES: NCCOP(=O)(O)OP(=O)(O)OC[C@H]1O[C@@H](n2ccc(N)nc2=O)[C@H](O)[C@@H]1O]

Molecular structures of CDP-DAG are provided below.

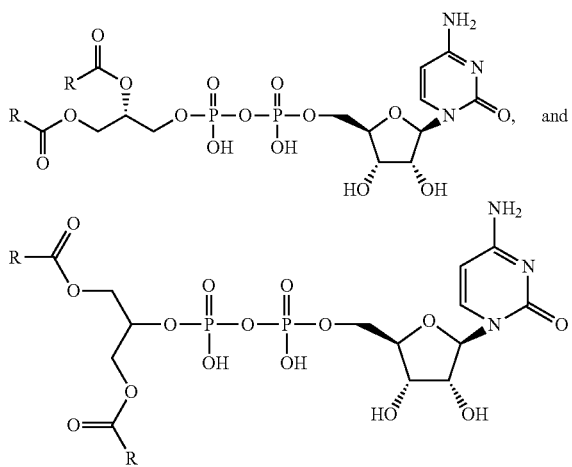

In these structures, R denotes points of attachment of various length fatty acid chains to the glycerol moiety of CDP-DAG.

In some embodiments, the CDP-CHO and/or CDP-ETH and/or CDP-DAG are present in equal concentrations or ratios. In some embodiments, at least two of the CDP-conjugated Plipid precursors are present in equal concentrations or ratios, which can be higher or lower than the third CDP-conjugated Plipid precursor, which may be absent. In some cases, one of the CDP-conjugated Plipid precursors is present at a concentration or ratio that is at least 2, 3, 4, 5, 6, 7, 8, 9, or 10 fold higher than one or both of the other CDP-conjugated Plipid precursors.

For example, in some embodiments, the composition for use in the disclosed methods contains CDP-CHO, CDP-ETH, and CDP-DAG in a molar ratio of about 1:1:1. In some embodiments, the composition for use in the disclosed methods contains CDP-CHO, CDP-ETH, and CDP-DAG in a molar ratio of about 1:1:2, 2:1:2, 3:1:2, 4:1:2, 5:1:2, 6:1:2, 7:1:2, 8:1:2, 9:1:2, 10:1:2, 1:1:3, 2:1:3, 3:1:3, 4:1:3, 5:1:3, 6:1:3, 7:1:3, 8:1:3, 9:1:3, 10:1:3, 1:1:4, 2:1:4, 3:1:4, 4:1:4, 5:1:4, 6:1:4, 7:1:4, 8:1:4, 9:1:4, 10:1:4, 1:1:5, 2:1:5, 3:1:5, 4:1:5, 5:1:5, 6:1:5, 7:1:5, 8:1:5, 9:1:5, 10:1:5, 1:1:6, 2:1:6, 3:1:6, 4:1:6, 5:1:6, 6:1:6, 7:1:6, 8:1:6, 9:1:6, 10:1:6, 1:1:7, 2:1:7, 3:1:7, 4:1:7, 5:1:7, 6:1:7, 7:1:7, 8:1:7, 9:1:7, 10:1:7, 1:1:8, 2:1:8, 3:1:8, 4:1:8, 5:1:8, 6:1:8, 7:1:8, 8:1:8, 9:1:8, 10:1:8, 1:1:9, 2:1:9, 3:1:9, 4:1:9, 5:1:9, 6:1:9, 7:1:9, 8:1:9, 9:1:9, 10:1:9, 1:1:10, 2:1:10, 3:1:10, 4:1:10, 5:1:10, 6:1:10, 7:1:10, 8:1:10, 9:1:10, 10:1:10, 2:1:1, 2:2:1, 2:3:1, 2:4:1, 2:5:1, 2:6:1, 2:7:1, 2:8:1, 2:9:1, 2:10:1, 3:1:1, 3:2:1, 3:3:1, 3:4:1, 3:5:1, 3:6:1, 3:7:1, 3:8:1, 3:9:1, 3:10:1, 4:1:1, 4:2:1, 4:3:1, 4:4:1, 4:5:1, 4:6:1, 4:7:1, 4:8:1, 4:9:1, 4:10:1, 5:1:1, 5:2:1, 5:3:1, 5:4:1, 5:5:1, 5:6:1, 5:7:8, 5:8:1, 5:9:1, 5:10:1, 6:1:1, 6:2:1, 6:3:1, 6:4:1, 6:5:1, 6:6:1, 6:7:1, 6:8:1, 6:9:1, 6:10:1, 7:1:1, 7:2:1, 7:3:1, 7:4:1, 7:5:1, 7:6:1, 7:7:1, 7:8:1, 7:9:1, 7:10:1, 8:1:1, 8:2:1, 8:3:1, 8:4:1, 8:5:1, 8:6:1, 8:7:1, 8:8:1, 8:9:1, 8:10:1, 9:1:1, 9:2:1, 9:3:1, 9:4:1, 9:5:1, 9:6:1, 9:7:1, 9:8:1, 9:9:1, 9:10:1, 10:1:1, 10:2:1, 10:3:1, 10:4:1, 10:5:1, 10:6:1, 10:7:1, 10:8:1, 10:9:1, 10:10:1, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, or 1:10:10.

The compositions disclosed can be used therapeutically in combination with a pharmaceutically acceptable carrier. By "pharmaceutically acceptable" is meant a material that is not biologically or otherwise undesirable, i.e., the material may be administered to a subject, along with the therapeutic agent or agents, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans or animals, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, stabilizing agents, surface active agents and the like in addition to the molecule of choice. Pharmaceutical compositions may also include one or more active ingredients, such as antimicrobial agents, anti-inflammatory agents, short- or long-acting β-adrenergic agonists, anesthetics, vaccine antigens, adjuvants, and DAMPs, Preparations for enteral and/or parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Enteral and parenteral vehicles include sodium chloride solution, Ringer's dextrose, dextrose and sodium chloride, lactated Ringer's, glucose, or fixed oils. Intravenous vehicles include fluid and nutrient replenishers, electrolyte replenishers (such as those based on Ringer's dextrose), and the like. Mucosal vehicles include sterile aqueous or non-aqueous solutions, suspensions, and emulsions. Examples include sodium chloride solution, Ringer's dextrose, dextrose and sodium chloride, lactated Ringer's, glucose, fixed oils, propylene glycol, and the like. Preservatives and other additives may also be present such as, for example, antimicrobials, anti-oxidants, chelating agents, and inert gases.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The herein disclosed compositions, including pharmaceutical composition, may be administered in a number of ways depending on whether the desired treatment is prophylactic use or for acute treatment of COPD and/or PF. For example, the disclosed compositions can be administered orally in powder or tablet form or given intravenously, intraperitoneally, intramuscularly, subcutaneously, intracavity, or transdermally. Pharmaceutical grade compositions may be administered orally as a compounded tablet including active ingredients at appropriate doses, excipients, and coatings for easing swallowing, and/or controlling release rate of active ingredients, and for shelf life extension. Pharmaceutical grade compositions may be administered orally as a liquid suspension or emulsion. Pharmaceutical grade compositions may be administered parenterally (e.g., intravenously with appropriate carriers, and stabilizers), by intramuscular injection, by intraperitoneal injection, transdermally, extracorporeally, ophthalmically, vaginally, rectally, intranasally, topically or the like, including topical intranasal administration or administration by inhalant.

In one embodiment, the disclosed compositions are administered in a dose equivalent to parenteral administration of about 0.1 ng to about 100 g per kg of body weight, about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of the disclosed compositions administered to achieve a therapeutic effective dose is about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The disclosed methods can be used in combination with other compositions and methods suitable for asthma subjects.

In some embodiments, the method further involves treating the subject with surfactant therapy. In some embodiments, the method further involves treating the subject with tracheal intubation, tracheotomy, tracheostomy, mechanical ventilation, with or without positive end-expiratory pressure (PEEP), prone or supine positioning, supplemental oxygen, nitric oxide, extracorporeal membrane oxygenation, β-adrenergic agonists or antagonists, corticosteroids and other anti-inflammatory agents, antibiotics, antiviral drugs, antifungal drugs, cytokines, stem cells from any source, intravenous fluids, whole blood or blood components, parenteral or enteral nutritional formulations, vasodilators, vasoconstrictors, diuretics, insulin or other synthetic or natural hormones, or any combination thereof, or any other treatments found to be beneficial in future experimental and/or clinical situations.

In some embodiments, the method further involves treating the subject with patient- or donor-derived cell-based therapies, including with embryonic stem cells (ESCs), mesenchymal stem cells (MSCs), induced pluripotent stem cells (iPSCs), and endothelial or epithelial progenitor cells. They are generally administered directly to the lung via intratracheal injection. ESCs, MSCs, and iPSCs are multipotent cells able to differentiate into a number of different cell lines and exert immunomodulatory, anti-proliferative, and anti-inflammatory effects. Endothelial and epithelial progenitor cells (including ATII cells) are more differentiated, but can replace damaged cells in the injured lung. Under experimental conditions, MSCs have been shown to transfer healthy mitochondria to injured lung cells, resulting in reversal of airway injury and have been shown to treat and prevent lung fibrosis in pre-clinical models.

In some embodiments, the method further involves treating the COPD or PF patient with a corticosteroid. For example, inhaled forms, such as fluticasone, can be used except in the case of severe persistent disease, in which oral corticosteroids may be needed. However, monotherapy with corticosteroids is generally not recommended for COPD patients.

In some embodiments, the method further involves treating the COPD or PF patient with supplemental (often ambulatory) oxygen to improve exercise tolerance.

In some embodiments, the method further involves treating the COPD or PF patient with antibiotics or antiviral agents of any class to ameliorate bacterial and viral co-infections that can cause acute disease exacerbations and hasten lung damage. Macrolides and fluoroquinolone antibiotics may also form part of a maintenance therapy regimen for COPD patients who experience frequent exacerbations and are refractory to standard care.

In some embodiments, the method further involves treating the subject with COPD with a bronchodilator. Bronchodilators alleviate bronchial obstruction and airflow limitation, reduce hyperinflation, and improve emptying of the lung and exercise performance. The three types of prescription bronchodilating drugs are ultra-long acting β-adrenergic agonists (Ultra-LABAs), long-acting β-adrenergic agonists (LABAs), and long-acting muscarinic antagonists (LAMAS). Ultra-LABAs, such as indacterol, olodaterol, and vilanterol are commonly taken daily, generally in combination with a long-acting muscarinic antagonist or inhaled corticosteroid. LABAs, such as salmeterol and formoterol, are commonly taken twice a day with an anti-inflammatory medication. LAMAS are taken daily, or twice daily, generally in combination with LABAs. Some examples of LAMAS are titropium bromide, glycopyrronium bromide, aclidinium bromide, umeclidinium bromide, and ipratropium bromide.

In some embodiments, the method further involves treating the subject with COPD with an oral phosphodiesterase inhibitor, such as roflumilast.

In some embodiments, the method further involves treating the subject with COPD with a mucolytic agent, such as N-acetyl cysteine, carbocysteine, or erdosteine, particularly during acute exacerbations.

In some embodiments, the method further involves treating the subject with PF using an antifibrotic agent, such as pirfenidone or nintenadib. While both agents show clinical benefit, they are also frequently associated with significant adverse events including gastrointestinal problems and photosensitivity.

In some embodiments, the method further involves treating the subject with one or more of classes of anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium).

A number of embodiments of the invention have been described. Nevertheless, it will be understood that various modifications may be made without departing from the spirit and scope of the invention. Accordingly, other embodiments are within the scope of the following claims.

EXAMPLES

Example 1

CDP-choline improved oxygenation. $S_aO_2$ increased from approximately 85% to approximately 96%. This is equivalent to an increase in $P_aO_2$ from approximately 65 mmHg to approximately 85 mmHg. It is also equivalent to an increase in $O_2$ carrying capacity of blood ($C_aO_2$) from approximately 88% to approximately 97% of normal. Patients with an $S_aO_2$ of 96% or a $P_aO_2$ of 96% would not require additional treatment CDP-choline improved cardiac function and resulted in better lung function and reduced pulmonary edema. Effects of single dose treatment late in infection are as good as those of daily treatment throughout course of infection.

Example 2

Table 2 shows the effect of CDP-conjugated precursor combinations.

Example 3

Figure 1:
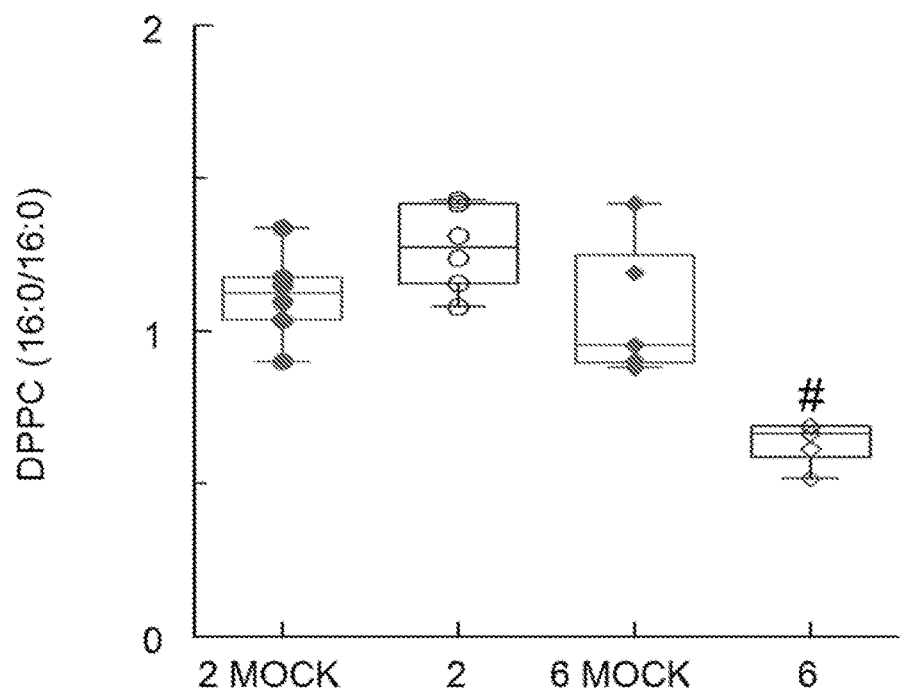
FIG. 1 is a plot showing effect of infection on ATII cell DPPC (16:0/16:0) surfactant. #=P<0.001.
Figure 2:
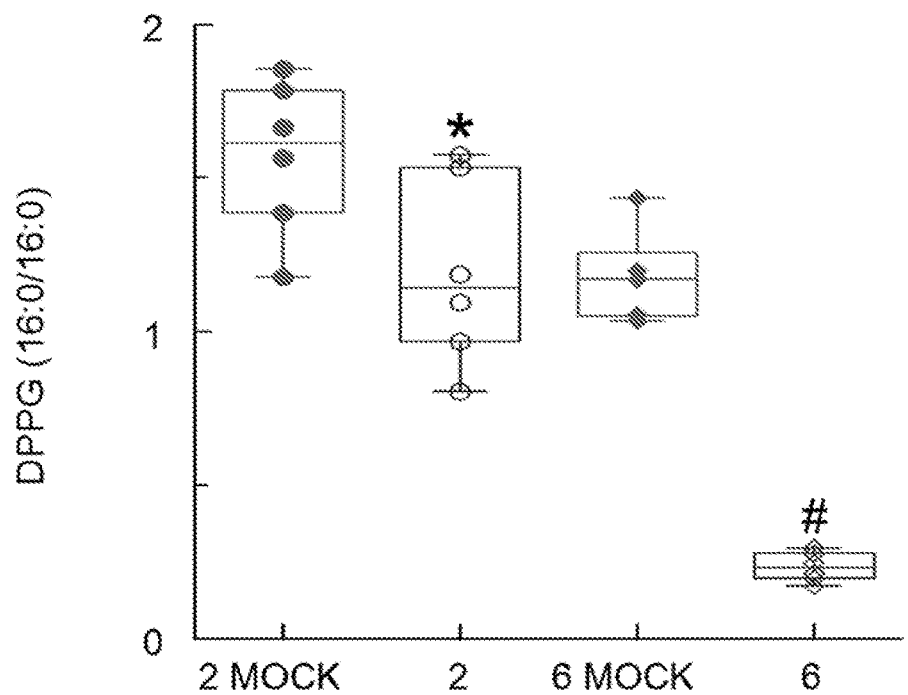
FIG. 2 is a plot showing effect of infection on ATII cell DPPG (16:0/16:0) surfactant. *=P<0.05, #=P<0.001.
Figure 3:
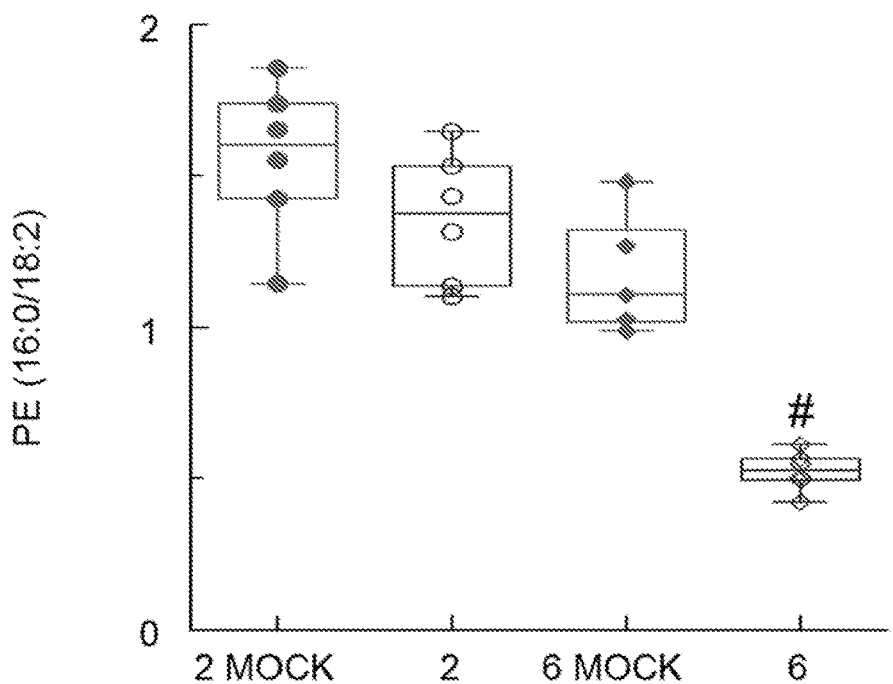
FIG. 3 is a plot showing effect of infection on ATII cell PE (16:0/18:2) surfactant. #=P<0.001.
Figure 4:
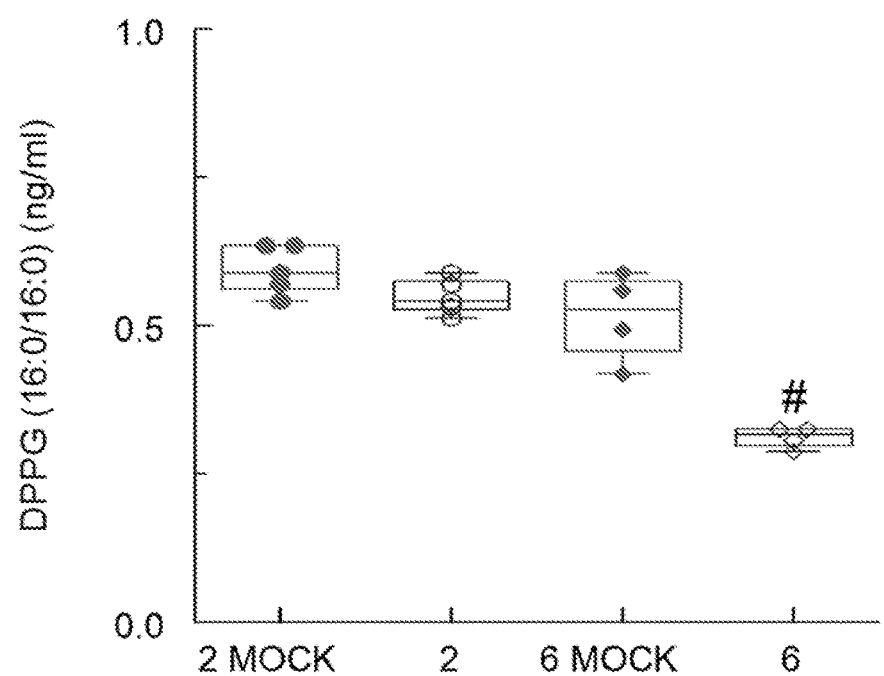
FIG. 4 is a plot showing effect of infection on BALF phospholipid glycerol. #=P<0.001.
Figure 5:
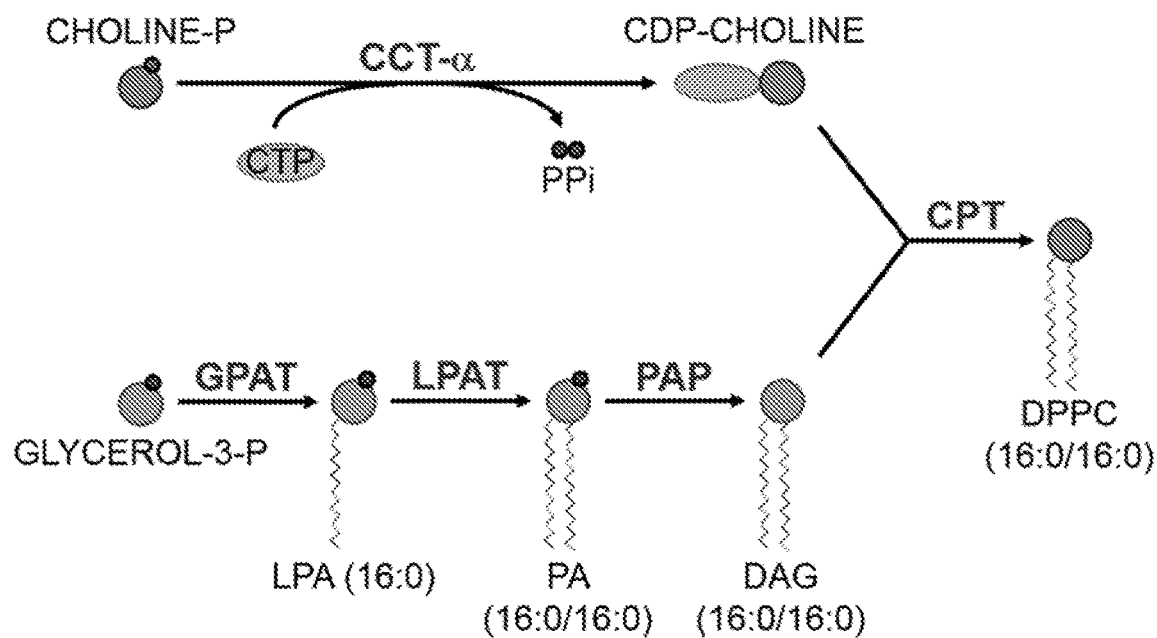
FIG. 5 is a schematic showing DPPC synthesis by the CDP-choline
(Kennedy) pathway.
Figure 6:
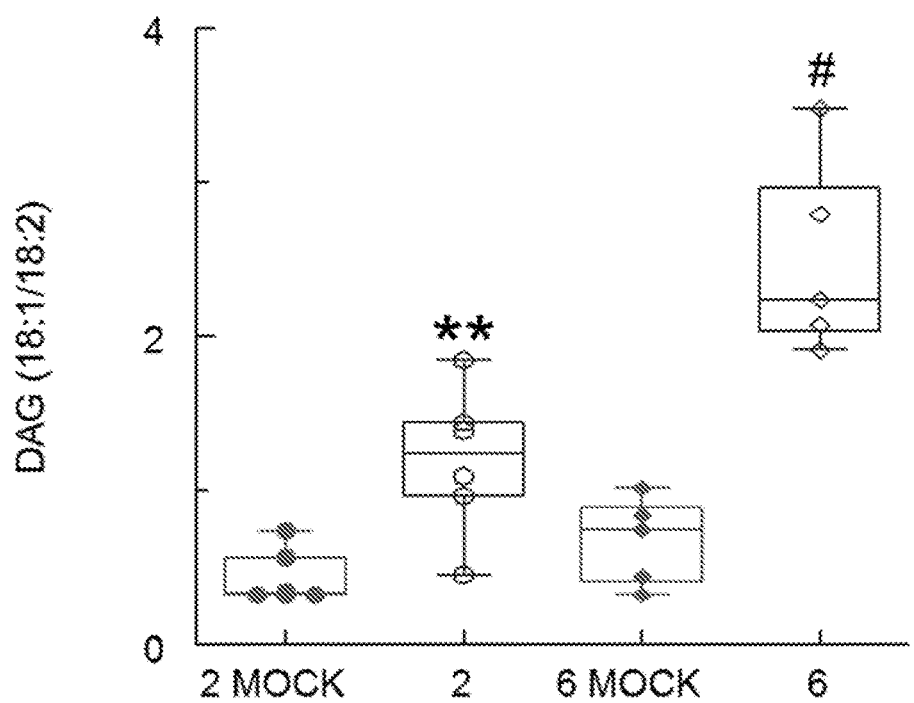
FIG. 6 is a plot showing effect of infection on ATII cell DAG (18:1/18:2). *=P<0.05, #=P<0.001.
Figure 7:
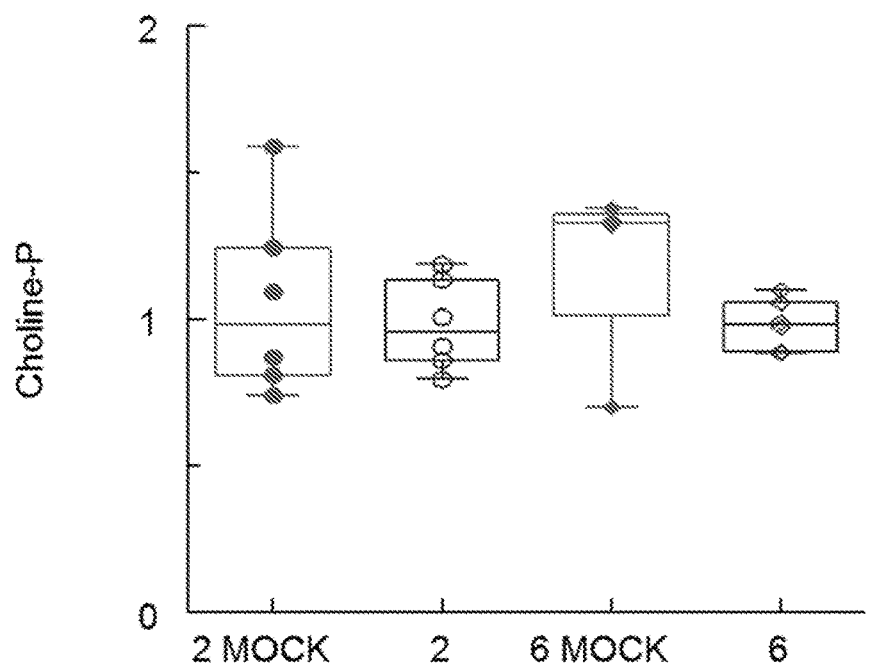
FIG. 7 is a plot showing effect of infection on ATII cell choline-P (18:1/18:2).
Figure 8:
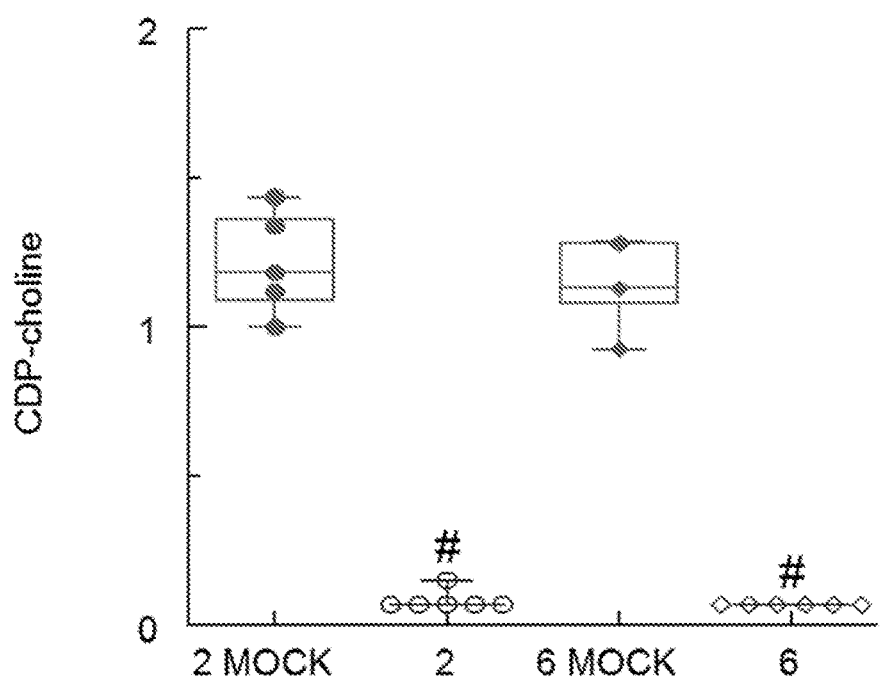
FIG. 8 is a plot showing effect of infection on ATII cell CDP-choline.
Figure 9:
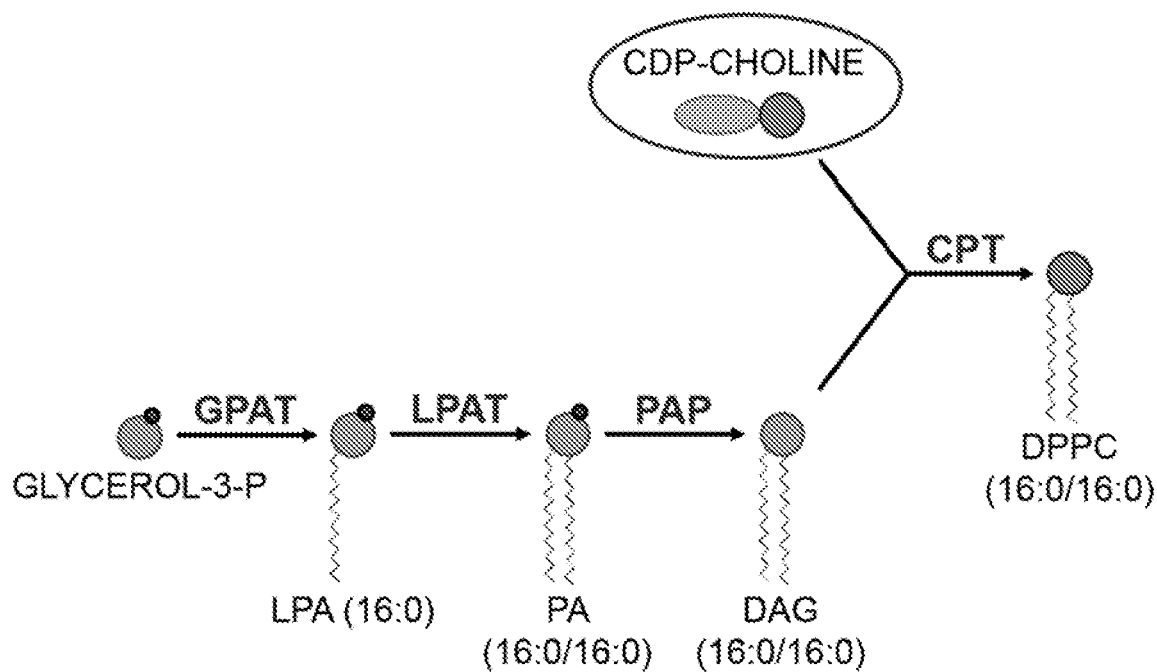
FIG. 9 is a schematic showing therapeutic approach.
Figure 10:
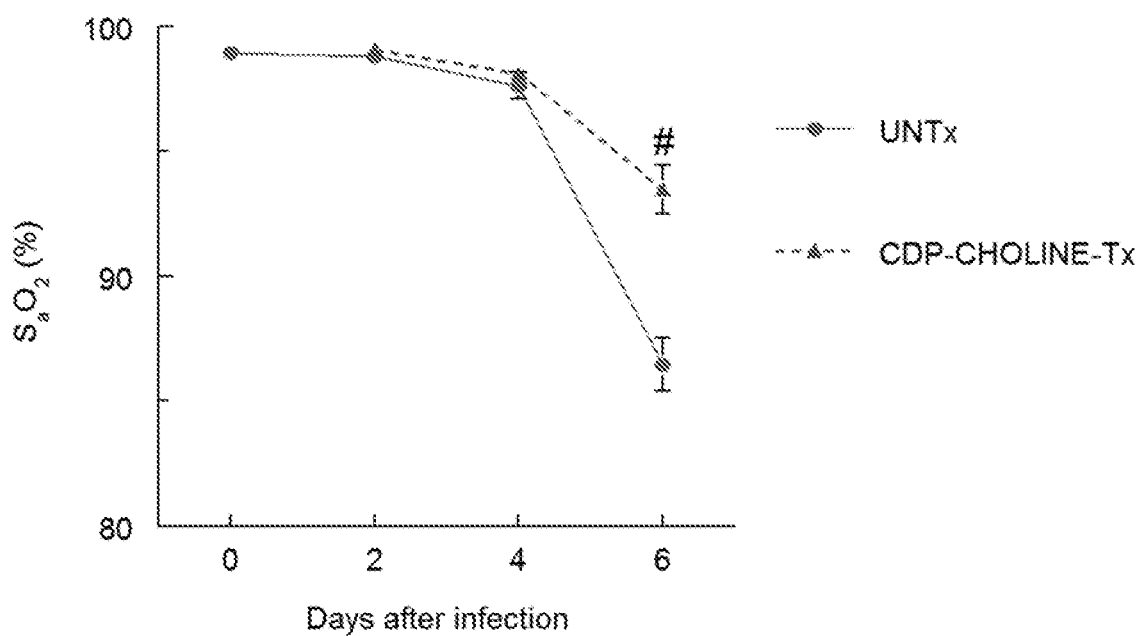
FIG. 10 is a graph showing effect of CDP-choline treatment (▲) on mouse $O_2$ SATS as a function of time (days after infection). #=P<0.001.
Figure 11:
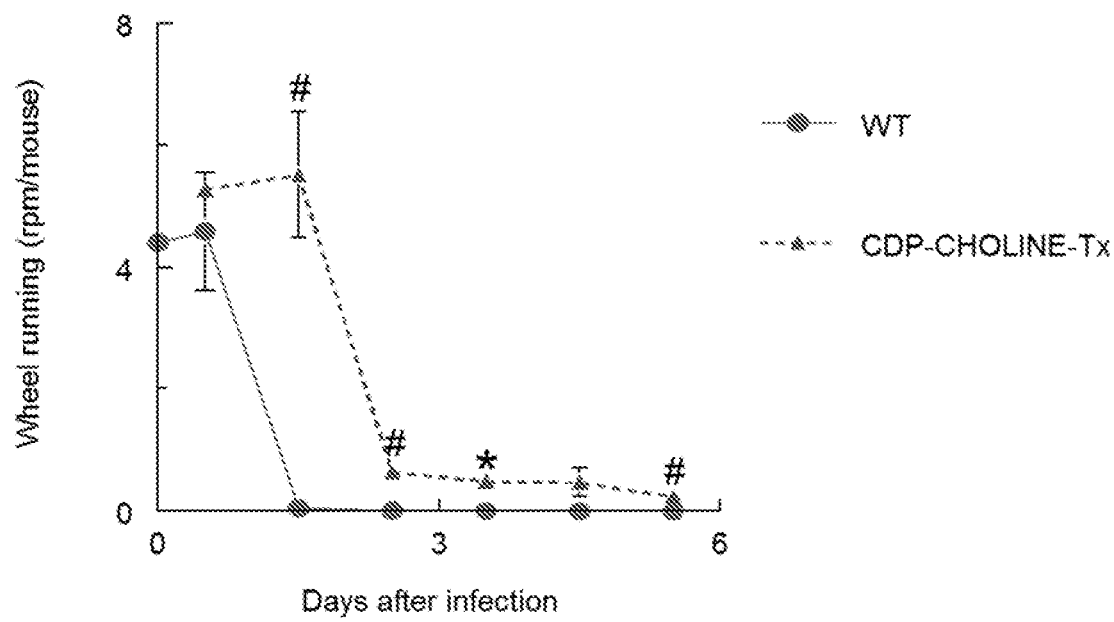
FIG. 11 is a graph showing effect of CDP-choline treatment (▲) on mouse activity (rmp/mouse) as a function of time (days after infection). *=P<0.05, #= P<0.001.
Figure 12:
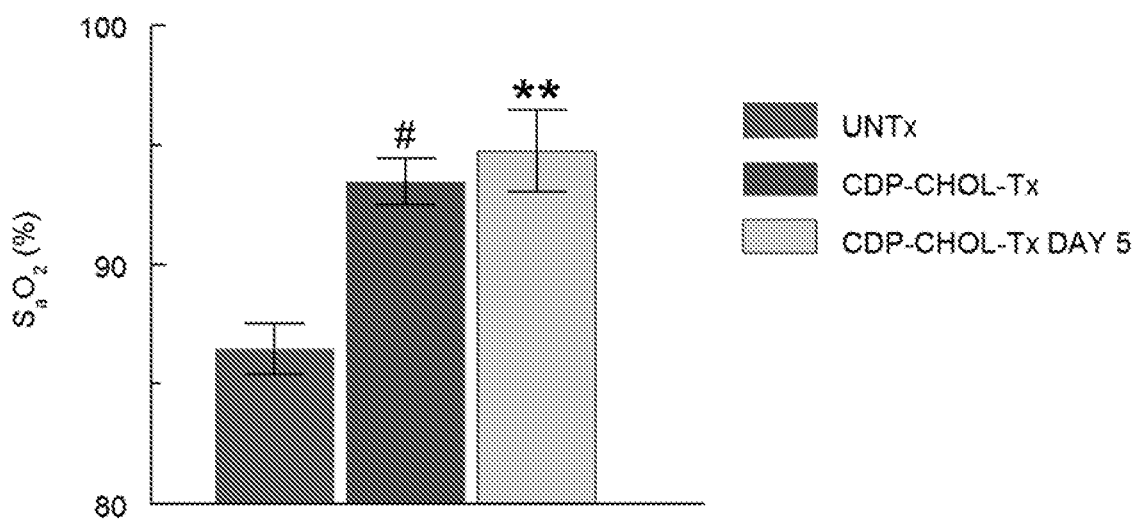
FIG. 12 is a bar graph showing effect of day 5 only CDP-choline treatment on mouse $O_2$ SATS. *=P<0.05, #=P<0.001.
Figure 13:
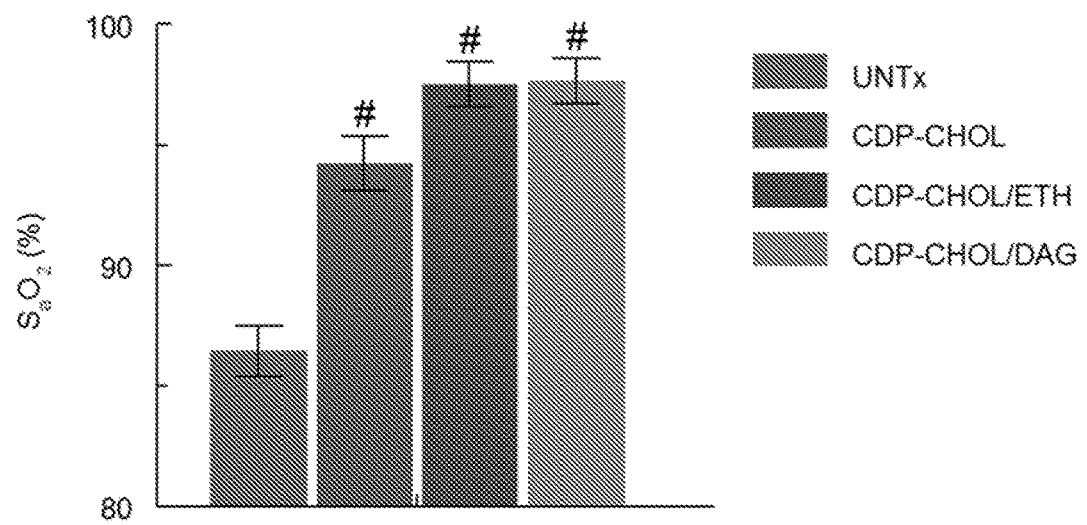
Figure 14:
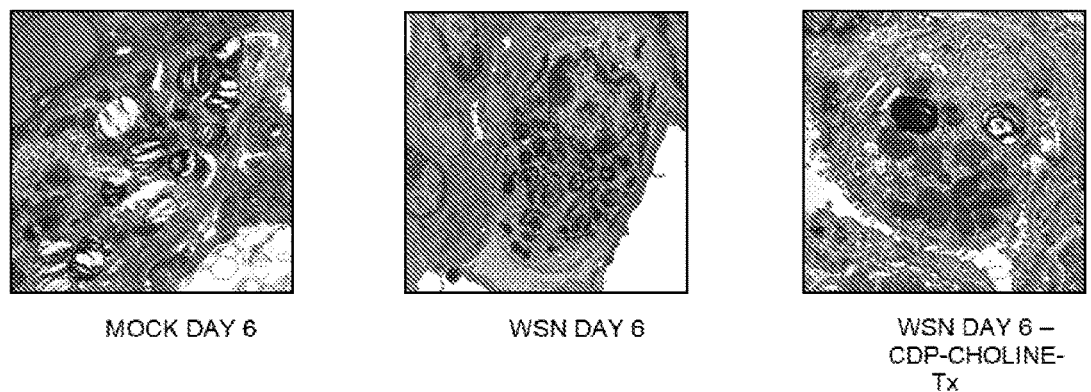

FIG. 14 is a group of three transmission electron micrographs showing effects of CDP-choline treatment on ultrastructure of ATII cell lamellar bodies (composed of surfactant lipids and proteins). Relative to mock-infected controls, lamellar bodies in ATII cells from influenza A/WSN/33 (H1N1)-infected mice are smaller and have disordered lamellae. CDP-choline treatment improves lamellar body morphology. Mi in ATII cells from CDP-choline-treated mice are also more electron-dense and have more normal cristae.

Example 4

Figure 15:
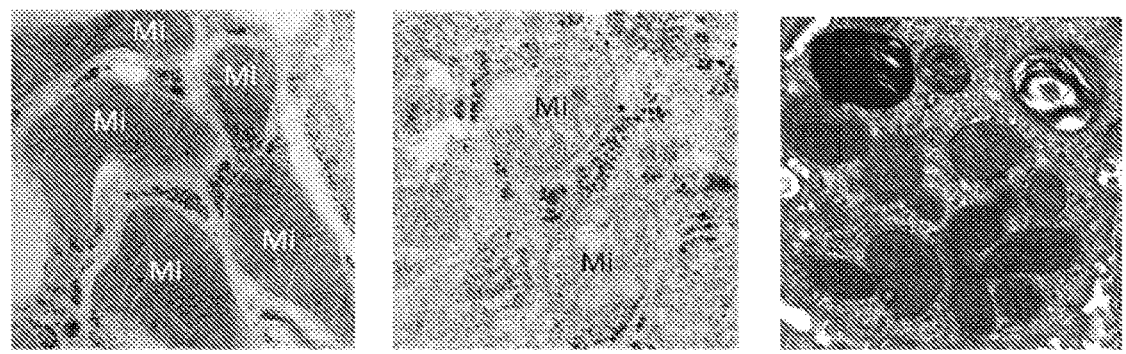

FIG. 15 is a group of 3 transmission electron micrographs showing effects of influenza infection on ultrastructure of ATII cell mitochondria (Mi). Relative to mock-infected controls (left), Mi in ATII cells from A/WSN/33 (H1N1)-infected mice (center) are fewer in number, less electron dense, and have disordered membranes and cristae. Mi in ATII cells from A/WSN/33 (H1N1)-infected mice treated with CDP-choline display normal morphology.

Example 5

Table 3 shows the effect of influenza infection and oral liponulceotide treatment on lung function.

Table 4 shows the effect of influenza infection and CDP-choline treatment on ATII cell ultrastructure.

Table 5 shows the effect of influenza infection and CDP-choline treatment on lung inflammation.

Table 6 shows the effect of influenza infection and CDP-choline treatment on mitochondrial function.

TABLE 2

Effect of influenza infection and i.p. liponucleotide treatment on lung function.

| | $S_aO_2$ (%) | HR (bpm) | WET:DRY | $R_{BASAL}$ | $C_{ST}$ |
|---|---|---|---|---|---|
| UNINFECTED | 99.0 ± 0.2 | 710 ± 10 | 4.2 ± 0.1 | 0.74 ± 0.03 | 0.1 ± 0.007 |
| DAY 6 MOCK CDP-CHO | 99.0 ± 0.2 | 730 ± 10 | — | 0.99 ± 0.03 | 0.05 ± 0.002 |
| DAY 6 UNTREATED | 86.5 ± 1.1 | 490 ± 10 | 7.1 ± 0.2 | 2.28 ± 0.17 | 0.04 ± 0.002 |
| DAY 6 CDP-CHO | 93.5 ± 1.0# | 570 ± 10* | 6.2 ± 0.4* | 1.96 ± 0.12 | 0.05 ± 0.002# |
| DAY 6 CDP-ETH | 91.1 ± 1.5 | 540 ± 20* | 6.5 ± 0.4 | — | — |
| DAY 6 CDP-DAG | 95.2 ± 1.6* | 600 ± 10** | 5.8 ± 0.1** | — | — |
| DAY 6 CDP-CHO + CDP-ETH | 97.5 ± 0.9# | 620 ± 10* | 6.9 ± 0.2 | — | — |
| DAY 6 CDP-CHO + CDP-DAG | 97.7 ± 0.9# | 600 ± 70 | 5.5 ± 0.2# | 1.54 ± 0.11* | 0.04 ± 0.02 |
| DAY 6 CDP-ETH + CDP-DAG | 78.7 ± 3.3 | 470 ± 40 | 6.7 ± 0.2 | — | — |
| DAY 6 CDP-CHO + CDP-ETH + CDP-DAG | 94.9 ± 1.1* | 620 ± 50* | 6.5 ± 0.9 | — | — |
| DAY 6 CDP-CHO ON DAY 5 ONLY | 92.9 ± 1.5* | 550 ± 10 | 6.2 ± 0.2 | 1.63 ± 0.22* | 0.05 ± 0.006* |

MOCK: Inoculated with virus diluent (0.1% FBS in normal saline)
CDP-CHO: CDP-choline (100 μg/mouse in 50 μl saline i.p., daily from 1-5 days post-infection or on day 5 only, as indicated)
CDP-ETH: CDP-ethanolamine (100 μg/mouse)
CDP-DAG: CDP-diacylglycerol (10 μg/mouse)
*P < 0.05,
**P < 0.005,
P < 0.001, vs. DAY 6 UNTREATED

TABLE 3

| | $S_aO_2$ (%) | HR (bpm) |
|---|---|---|
| UNINFECTED | 99.0 ± 0.2 | 710 ± 10 |
| DAY 6 UNTREATED | 86.5 ± 1.1 | 490 ± 10 |
| DAY 6 SALINE VEHICLE-TREATED | 87.1 ± 2.8 | 460 ± 20 |
| DAY 6 CDP-CHO + CDP-DAG | 91.9 ± 2.6(*) | 570 ± 40* |

CDP-CHO + CDP-DAG: CDP-choline (100 μg/mouse) + CDP-diacylglycerol (10 μg/mouse) by oral gavage, daily from 1-5 days post-infection
(*)P = 0.0516,
*P < 0.05, vs. DAY 6 UNTREATED

TABLE 4

| | DAY 6 MOCK | DAY 6 UNTREATED | DAY 6 FLU + CDP-CHO |
|---|---|---|---|
| ATII CELL AREA (μm²) | 30.37 ± 2.98 | 72.04 ± 3.63 | 53.64 ± 5.63* |
| LAMELLAR BODIES/CELL | 14.27 ± 1.32 | 12.05 ± 0.93 | 8.1 ± 1.16* |
| LAMELLAR BODY AREA (μm²) | 0.47 ± 0.06 | 0.59 ± 0.44 | 0.41 ± 0.04* |
| MITOCHONDRIAL/CELL | 16 ± 2.31 | 17.75 ± 2.85 | 14.5 ± 1.78* |
| MITOCHONDRIAL AREA (μm²) | 0.43 ± 0.02 | 0.2 ± 0.01 | 0.34 ± 0.01* |

CDP-CHO: CDP-choline (100 μg/mouse in 50 μl saline i.p., daily from 1-5 days post-infection)
*P < 0.05, vs. day 6 untreated

TABLE 5

| | DAY 6 MOCK | DAY 6 UNTREATED | DAY 6 FLU + CDP-CHO |
|---|---|---|---|
| BALF ALVEOLAR MACS (×10⁶/ml) | — | 2.67 ± 0.51 | 1.08 ± 0.21* |
| BALF NEUTROPHILS (×10⁶/ml) | — | 1.69 ± 0.16 | 0.45 ± 0.07** |
| BALF PC | — | 0.79 ± 0.12 | 1.61 ± 0.45* |
| VIRAL TITER (log PFU/g) | 0 | 5.32 ± 0.07 | 5.32 ± 0.07 |

CDP-CHO: CDP-choline (100 μg/mouse in 50 μl saline i.p., daily from 1-5 days post-infection)
*P < 0.05
**P < 0.005,
: P < 0.001, vs. day 6 untreated

TABLE 6

| | DAY 6 MOCK | DAY 6 UNTREATED | DAY 6 FLU + CDP-CHO |
|---|---|---|---|
| MITOCHONDRIAL ATP PRODUCTION | 40.54 ± 4.91 | 20.36 ± 1.3 | 36.91 ± 6.82# |
| mitochondrial membrane POTENTIAL ($\Psi_m$; DilC$_1$(5) MCF) | 12.29 ± 0.42 | 6.89 ± 0.38 | 10.14 ± 2.3* |

CDP-CHO: CDP-choline (100 μg/mouse in 50 μl saline i.p., daily from 1-5 days post-infection)
*P < 0.05,
**P < 0.005,
P < 0.001, vs. day 6 untreated Example 6

Experimental Design

To experimentally determine the efficacy of the liponucleotides (lipoNTs) CDP-choline (CDP-CHO), CDP-ethanolamine (CDP-ETH), and CDP-diacylglycerol 16:0/16:0 (CDP-DAG) as therapeutics in a mouse model of emphysema (intratracheal elastase administration) (Yoshida S, et al. Am J Physiol Lung Cell Mol Physiol 2012 303:L852-L860).

To induce emphysema, porcine pancreatic elastase was administered intratracheally to adult female C57BL/6 mice (n=5-10 per group) by per os intubation under light anesthesia at day 0 and day 7. LipoNTs were administered daily by the intraperitoneal route in 50 μl sterile saline at the timepoints indicated for each group.

The following experimental groups were generated:
1. Normal mice (no elastase administration or lipoNT treatment).
2. Elastase administration (1.5 U/mouse) only (no lipoNT treatment).
3. DRA+CDP-CHO (5 mg/kg) treatment from days 1-13.
4. DRA+CDP-CHO+CDP-ETH (5 mg/kg) treatment from days 1-13.
5. DRA+CDP-CHO+CDP-DAG (0.5 mg/kg) treatment from days 1-13.
6. DRA+CDP-CHO+CDP-ETH+CDP-DAG treatment from days 1-13.
7. DRA+CDP-CHO+CDP-ETH treatment from days 8-13.
8. DRA+CDP-CHO+CDP-DAG treatment from days 8-13.

Analysis of elastase and lipoNT effects: Data were collected 14 days after first elastase administration in terminal experiments.

1. Static lung compliance (CST) was measured in live mice by the forced-oscillation method using the SciReq flexiVent computer-controlled mechanical ventilator, as in previous studies (Traylor Z P, Yet al. Am J Physiol Lung Cell Mol Physiol 2010 298:L437-L445).
2. Following flexiVent analysis, bronchoalveolar lavage was performed on all mice using 0.8 ml PBS. BALF total and differential cell counts (trypan-blue stained live cells and Giemsa-stained cytospins, respectively) were performed on cell pellets to assess inflammatory cell infiltrates. BALF alveolar macrophage (AM) counts were determined.

Summary

Figure 16:
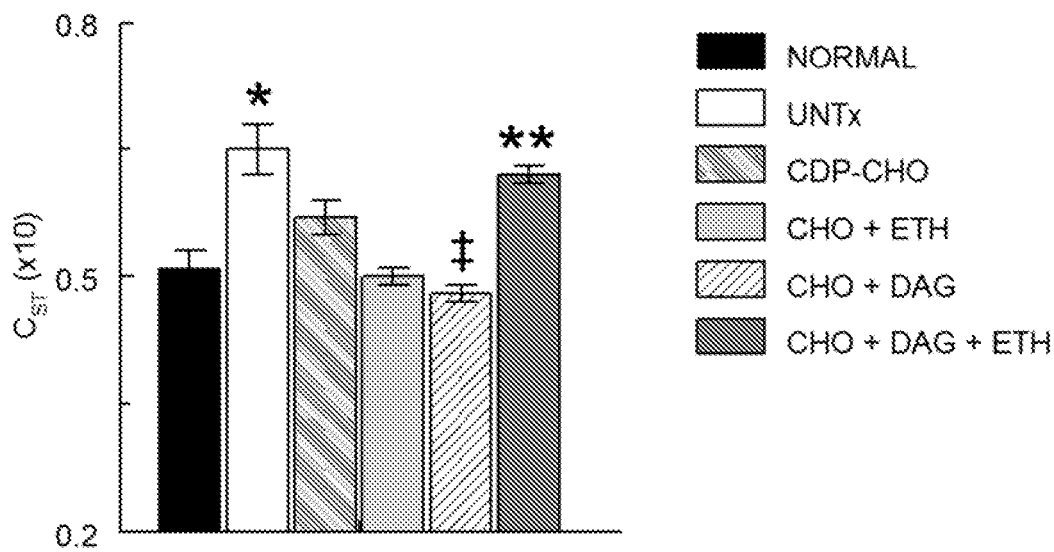
Figure 18:
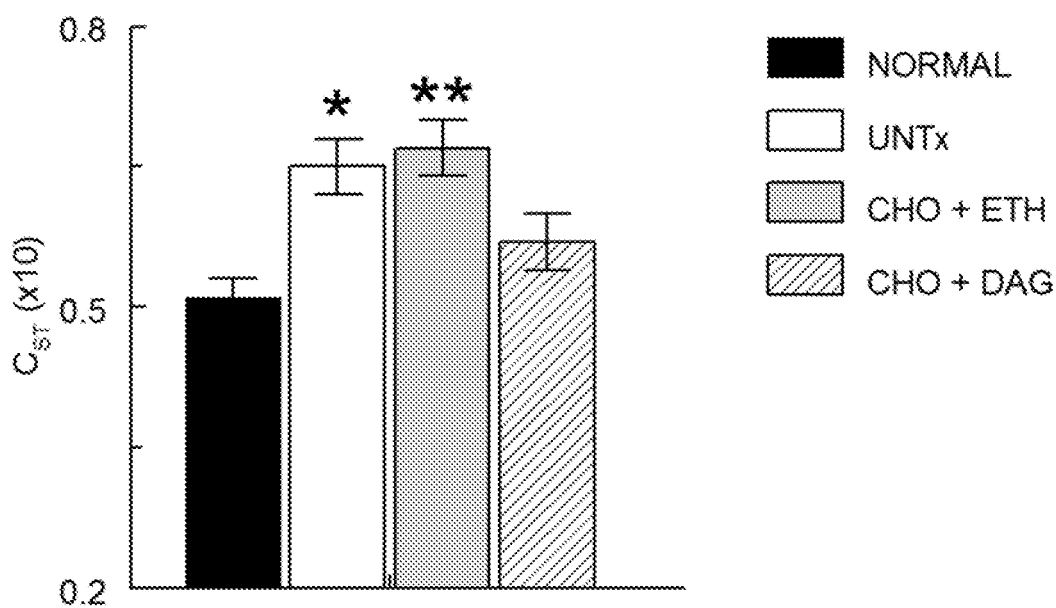

Administration of elastase results in a significant increase in static lung compliance (CST) (FIGS. 16 and 18), which indicates alveolar destruction and presence of emphysema. Treatment with CDP-CHO throughout the course of emphysema development (days 1-13) decreases CST and co-administration of CDP-ETH or CDP-DAG with CDP-CHO results in normalization of CST. Effects of CDP-CHO+CDP-DAG on CST are significantly greater than those of CDP-CHO alone. However, co-treatment with all 3 lipoNTs has no beneficial effects on CST. Treatment with a combination of CDP-CHO+CDP-DAG (but not CDP-CHO+CDP-ETH) after the second dose of elastase (i.e., from day 8) also decreases CST towards normal.

Figure 17:
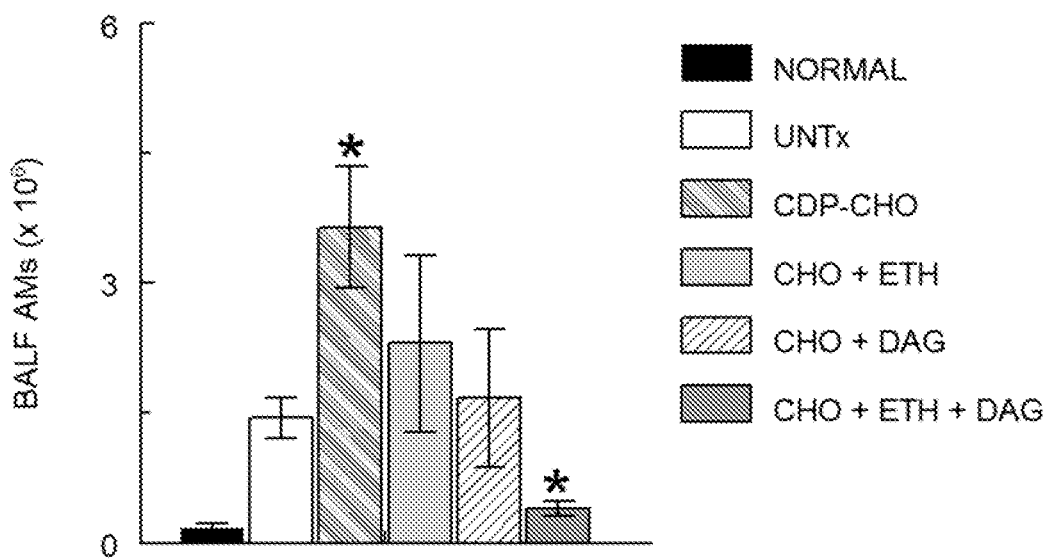
Figure 19:
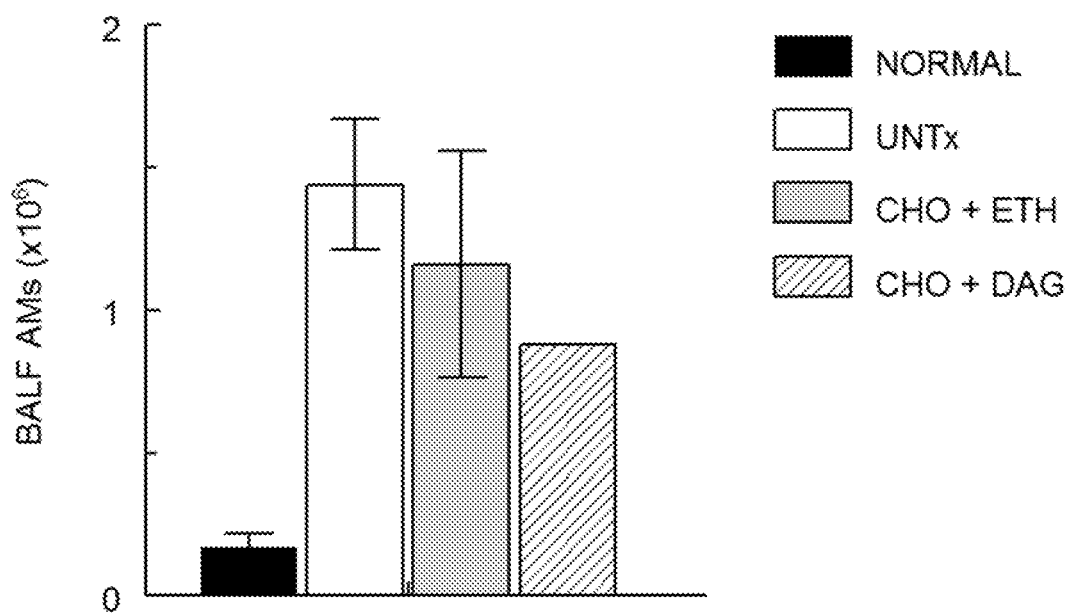
Figure 20:
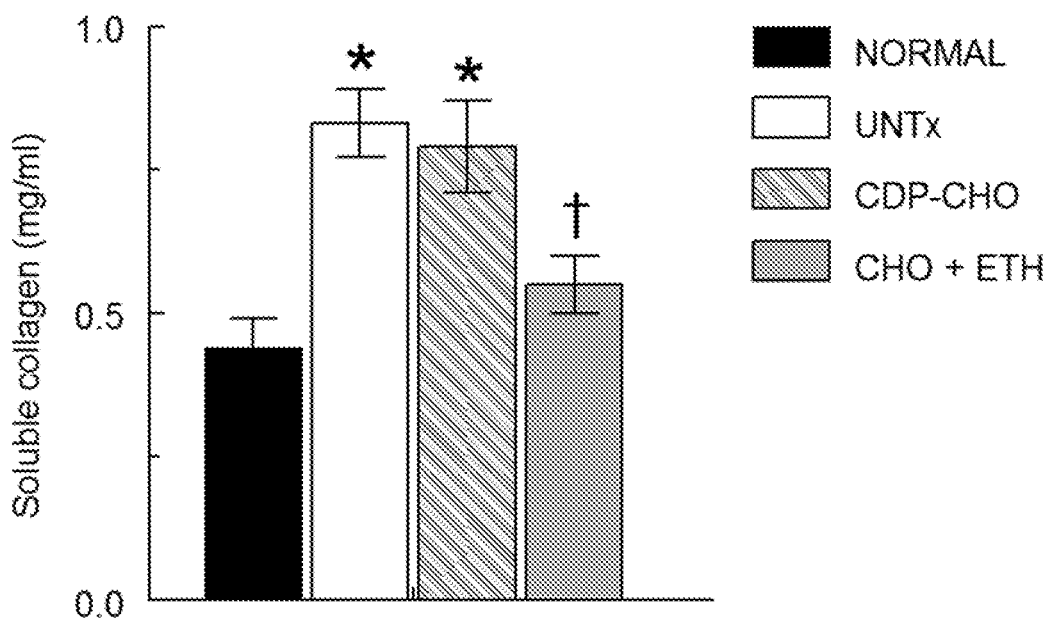
Figure 21:
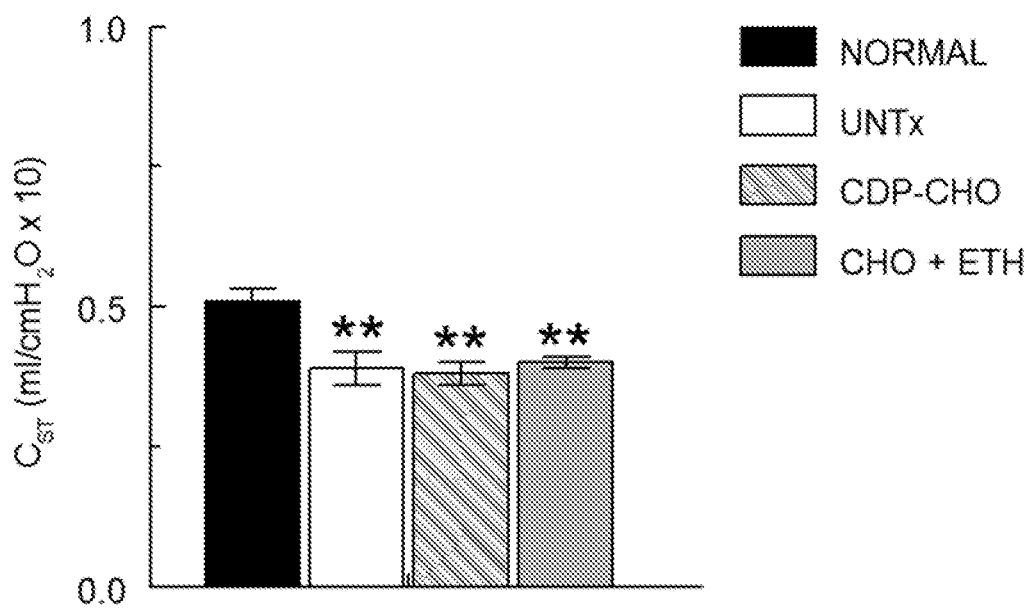
Figure 22:
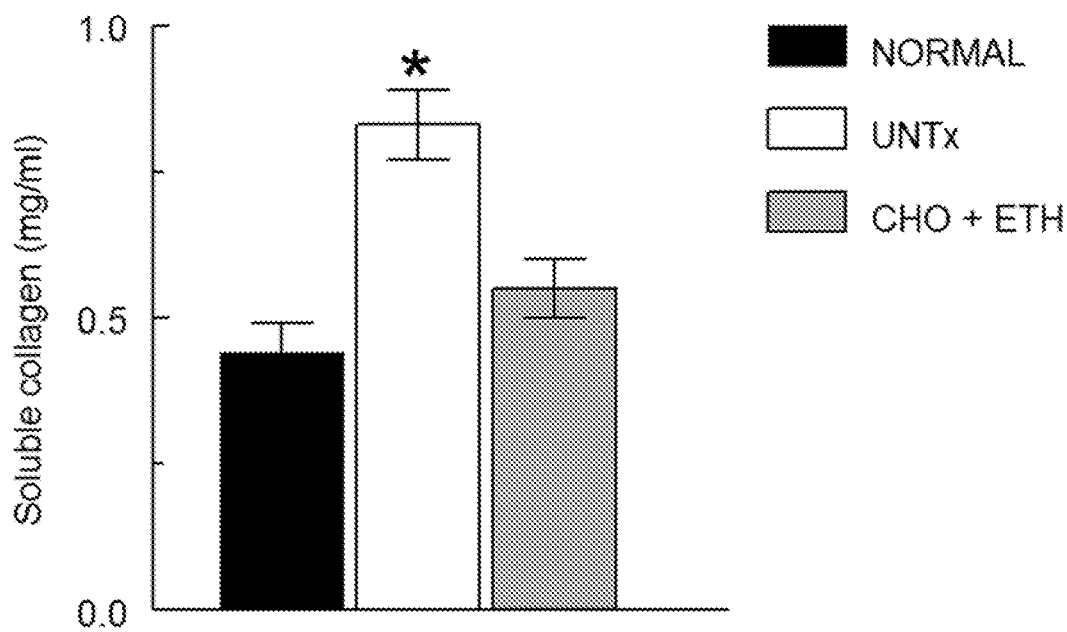
Figure 23:
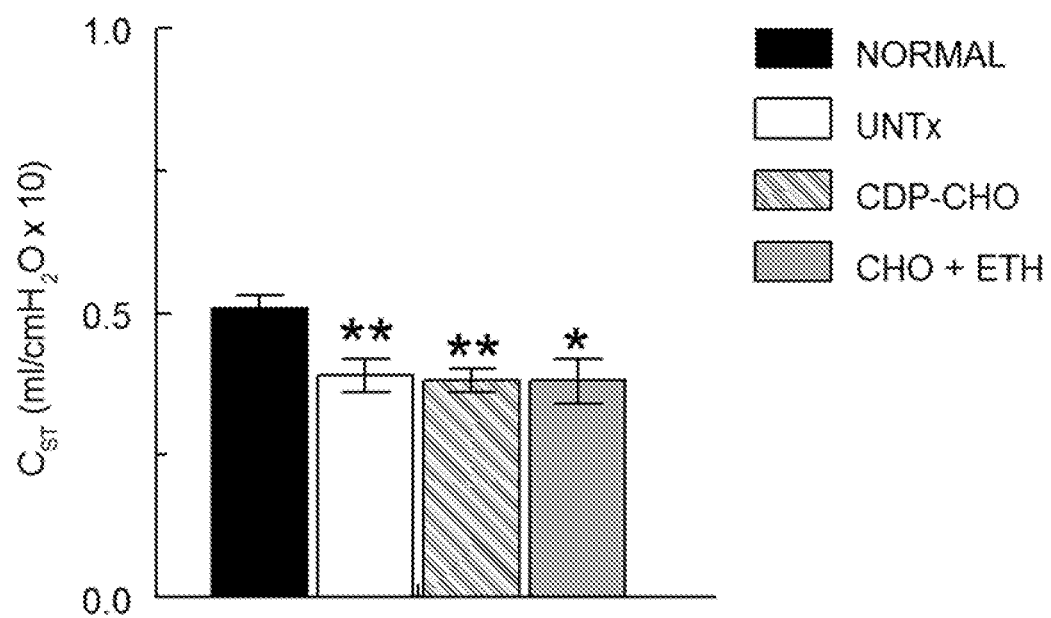

Elastase administration results in increased BALF AMs, indicative of ongoing inflammation (FIGS. 17 and 19). This effect is enhanced by treatment with CDP-CHO throughout the course of emphysema development (days 1-13) but is abrogated by co-treatment with all 3 lipoNTs over this timecourse. Later lipoNT treatment has no significant impact on BALF AMs.

Conclusions

Overall, the most significant beneficial effects of lipoNT are seen when mice with elastase-induced emphysema are treated with CDP-CHO+CDP-DAG from days 1-13 or from days 8-13: these regimens result in normalization of CST and do not increase leukocyte infiltrates into the lung.

Example 2

Experimental Design

Aim:

To experimentally determine the efficacy of the liponucleotides (lipoNTs) CDP-choline (CDP-CHO), CDP-ethanolamine (CDP-ETH), and CDP-diacylglycerol 16:0/16:0 (CDP-DAG) as therapeutics in a mouse model of pulmonary fibrosis (bleomycin exposure) (Chung S, et al. Oncotarget 2016 7:17532-17546).

Protocol:

To induce emphysema, bleomycin (BLEO) was administered intratracheally to adult female C57BL/6 mice (n=5-10 per group) by per os intubation under light ketamine/xylazine anesthesia at day 0. LipoNTs were administered daily by the intraperitoneal route in 50 μl sterile saline at the timepoints indicated for each group.

The following experimental groups were generated:
1. Normal mice (no BLEO or lipoNT treatment).
2. BLEO administration (0.01 mg/mouse) only (no lipoNT treatment).
3. BLEO+CDP-CHO (5 mg/kg) treatment from days 1-20.
4. BLEO+CDP-CHO+CDP-ETH (5 mg/kg) treatment from days 1-20.

5. BLEO+CDP-CHO+CDP-DAG (0.5 mg/kg) treatment from days 1-20.

6. BLEO+CDP-CHO+CDP-ETH+CDP-DAG treatment from days 1-20.

7. BLEO+CDP-CHO+CDP-ETH treatment from days 8-20.

8. BLEO+CDP-CHO+CDP-DAG treatment from days 8-20.

9. BLEO+CDP-CHO+CDP-ETH treatment from days 15-20.

10. BLEO+CDP-CHO+CDP-DAG treatment from days 15-20.

Analysis of BLEO and lipoNT Effects:

Data were collected 21 days after first exposure to BLEO in terminal experiments.

1. Mortality rate.

2. Carotid arterial $O_2$ saturation ($S_aO_2$) and heart rate were measured in conscious individually-identified animals by pulse oximetry using the MouseOx system.

3. Static lung compliance (CST) was measured in live mice by the forced-oscillation method using the SciReq flexiVent computer-controlled mechanical ventilator, as in previous studies (Traylor Z P, et al. Am J Physiol Lung Cell Mol Physiol 2010 298:L437-L445).

4. Following flexiVent analysis, lungs were removed and flash frozen in liquid N2 for analysis of collagen content. Soluble collagen was measured by a standard Sircol assay.

Results

As shown in Table 7 and FIGS. 20 to 23, daily treatment with CDP-CHO from 1-20 days after BLEO significantly attenuated BLEO-induced mortality but had no other beneficial effects in this model of pulmonary fibrosis. Treatment with a combination of CDP-CHO+CDP-ETH from days 1-20 or days 8-20 reduced both mortality and BLEO-induced collagen deposition at 21 days. However, treatment with CDP-CHO+CDP-ETH had no beneficial effect on BLEO-induced reductions in CST. No treatment altered $S_aO_2$ at day 21, although this was not depressed in UNTx mice at this timepoint. Finally, all treatments that included CDP-DAG resulted in high levels of mortality.

Conclusions

Overall, the most significant beneficial effects of lipoNT are seen when mice with BLEO-induced pulmonary fibrosis are treated with CDP-CHO+CDP-ETH, either from immediately post-insult or during the early phases of fibrosis: this regimen results in both attenuation of mortality and reduced collagen deposition in the lung, although its effects were not reflected in an improvement in lung function.

TABLE 7

| TREATMENT | Mortality | SaO2 (%) | Collagen (mg/ml) | CST (ml/cmH2O ×10) |
|---|---|---|---|---|
| NONE | — | — | 0.44 ± 0.05 | 0.51 ± 0.02 |
| BLEO ONLY | 60% | 98.3 ± 0.4 | 0.83 ± 0.06 | 0.39 ± 0.03 |
| BLEO + CHO D1-20 | 20% | 97.0 ± 1.0 | 0.79 ± 0.08 | 0.38 ± 0.02 |
| BLEO + CHO + ETH D1-20 | 10% | 98.9 ± 0.1 | 0.55 ± 0.04*† | 0.4 ± 0.01 |
| BLEO + CHO + DAG D1-20 | 100% | — | — | — |
| BLEO + CHO + ETH + DAG D1-20 | 100% | — | — | — |
| BLEO + CHO + ETH D8-20 | 40% | 99.3 ± 0.1 | 0.52 ± 0.03*† | 0.38 ± 0.04 |
| BLEO + CHO + DAG D8-20 | 100% | — | — | — |
| BLEO + CHO + ETH D15-20* | 80% | — | — | — |
| BLEO + CHO + DAG D15-20* | 60% | — | — | — |

Data shown as mean ± SEM.
*Due to high mortality rate no statistically-meaningful data could be derived from the small number of survivors.
*P < 0.05, vs. BLEO ONLY.
†P < 0.05, vs. BLEO + CHO D1-20.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating chronic obstructive pulmonary disease (COPD) and/or pulmonary fibrosis (PF) in a subject, comprising administering to the subject an effective amount of a composition consisting essentially of one or more cytidine diphosphate (CDP)-conjugated precursors in a pharmaceutically acceptable carrier, wherein the CDP-conjugated precursors are selected from the group consisting of CDP-choline (CDP-CHO), CDP-ethanolamine (CDP-ETH), CDP-diacylglycerol (CDP-DAG), and combinations thereof.

2. The method of claim 1, wherein the composition comprises two or more CDP-conjugated phospholipid precursors.

3. The method of claim 2, wherein the composition comprises CDP-CHO and CDP-DAG.

4. The method of claim 2, wherein the composition comprises CDP-CHO and CDP-ETH.

5. The method of claim 3, wherein the CDP-CHO and CDP-DAG or CDP-CHO and CDP-ETH are present in equal concentrations.

6. The method of claim 2, wherein the composition comprises CDP-CHO, CDP-ETH, and CDP-DAG.

7. The method of claim 6, wherein the CDP-CHO, CDP-ETH, and CDP-DAG are present in equal concentrations.

8. The method of claim 2, wherein the CDP-conjugated phospholipid precursors are collectively present at a concentration of at least 0.1 ng per kg of body weight.

9. The method of claim 1, wherein the CDP-conjugated phospholipid precursors comprise one or more chemical modification selected from the group consisting of methylation, esterification, amidation, nitration, nitrosylation, oxidation, sulfation, acetylation, alcoholysis, acidolysis, biotinylation, and fluorophore conjugation.

* * * * *